United States Patent [19]
Kaluza et al.

[11] Patent Number: 6,005,658
[45] Date of Patent: Dec. 21, 1999

[54] INTERMITTENT MEASURING OF ARTERIAL OXYGEN SATURATION OF HEMOGLOBIN

[75] Inventors: Michael Kaluza, Rohrau; Michael Blank, Boelingen, both of Germany

[73] Assignee: Hewlett-Packard Company, Palo Alto, Calif.

[21] Appl. No.: 08/878,890

[22] Filed: Jun. 19, 1997

[51] Int. Cl.⁶ .................................................. G01N 33/48
[52] U.S. Cl. .................................. 356/39; 356/41; 356/42
[58] Field of Search ................................... 356/39, 41, 42

[56] References Cited

U.S. PATENT DOCUMENTS 5,595,176   1/1997   Yamaura ..................................... 356/41
5,673,694   10/1997  Rivers ........................................ 356/41

Primary Examiner—Frank G. Font
Assistant Examiner—Reginald A. Ratliff

[57] ABSTRACT

Described is a method and a system for detecting the arterial oxygen saturation of hemoglobin (also called blood oxygenation, SpO2 or SaO2 measuring), comprising a measuring device for performing a blood oxygenation measurement and a controller unit. The measuring device is controllable by the controller unit so that the blood oxygenation measurement can be performed non-continuously. In a first step the measuring device is powered on, in a second step the blood oxygenation measurement is performed, and in a third step the measuring device or parts thereof are powered down, whereby the three steps are repeatable periodically. This provides SpO2 measurement applicable in telemetric or handhold instruments. The system is preferably used in telemetric or handhold instruments.

24 Claims, 1 Drawing Sheet

INTERMITTENT MEASURING OF ARTERIAL OXYGEN SATURATION OF HEMOGLOBIN

BACKGROUND OF THE INVENTION

The present invention generally relates to pulse oximeters, the use thereof, and/or a method for detecting blood oxygenation.

Pulse oximeters typically measure and display various blood flow characteristics including—but not limited thereto—blood oxygen saturation of hemoglobin in arterial blood, the rate of blood pulsations corresponding to the heart rate of the patient, or a perfusion indicator.

Pulse oximeters generally determine the arterial oxygen saturation of hemoglobin (also called SpO2 or SaO2 measurement) by way of a non-invasive technique using two different monochromatic light sources, which are typically formed by LEDs. Normally one of the LEDs emits light in the red wavelength range of about 645 nm and the other one in the infrared wavelength range of 940 nm. The light emitted by both LEDs is transmitted through a predetermined area of the patient's body.

Typically, pulse oximeter systems utilize an oxygen saturation sensing probe which is arranged to be detachably secured to the patient's finger. Usually, the probe has the form of a clip including both light emitting diodes and a light detector. The probe is arranged such that the light of both light emitting diodes having passed the predetermined area of the patient's body is received by a single light detector. An example for a pulse oximeter is the Hewlett Packard Component Monitoring System with the Pulse Oximeter Module, the 'HP M1020A'.

As it is known in the art of pulse oximetry, the light of both light sources is attenuated by static and dynamic absorbers on its path through the patient's body to the light detector. The arterial blood whose quantity varies with the time synchronously with the patient's heartbeat represents the only dynamic absorber during the pulse period. All other absorbers, such as skin, tissue or bone, are not time-variant. Thus, pulse oximeters make use of the pulsatile component of arterial blood generated by the heartbeat at only two spectral lines.

The light detector, which may have the form of a photo diode, receives the modulated light intensities of each wavelength. Then, these signals are usually amplified, low pass filtered, converted from analog to digital and further processed, e.g., in a microprocessor system. A pulse finding algorithm analyses the received signals which are so-called spectrophotometric signals for identifying the pulses and for determining the pulse. After identifying the pulse period, the microprocessor system determines the diastolic and systolic values of the spectrophotometric signals and derives therefrom the so-called relative absorption ratios. Subsequently, the microprocessor system computes in a saturation calculation algorithm the arterial oxygen saturation from the relative absorption ratio using calibration data and so-called extinction coefficients from the absorption spectrum of hemoglobin and oxyhemoglobin at the appropriate wavelengths. The mathematical background therefor, which makes use of Lambert-Beer's law, has been described in sufficient detail in a multiplicity of former publications. See, for example, EP-A-262 778 which contains a rather good breakdown of the theory.

Since the early 1980s, when pulse oximetry was introduced, this non-invasive method of monitoring the arterial oxygen saturation level in a patient's blood (SpO2) has become a standard method in the clinical environment because of its simple application and the high value of the information applicable to nurses and doctors. It has become as common in patient monitoring to measure the oxygen level in the blood as to monitor heart activity with the ECG. In some application areas, like anesthesia in a surgical procedure, it is mandatory for doctors to measure this vital parameter.

Background information about pulse oximetry is given by S. Kästle et al., "A New Family of Sensors for Pulse Oximetry", Hewlett-Packard Journal, February 1997, pages 39–53.

In recent time, patient monitoring has been expanded from pure stationary monitoring with stationary instruments, e.g., on intensive care units, to non-stationary monitoring comprising smaller and mobile instruments such as telemetry or handhold instruments. Telemetry systems, such as an Hewlett Packard 'HP M1403A Digital Telemetry System', consist of a telemetric transmitter (like an Hewlett Packard 'HP M1400A pocket sized UHF Transmitter') with embedded measurement devices, such as ECG or SpO2. The transmitter is battery driven and carried around by a stationary or ambulating patient. The measurement signal is transmitted via UHF to a central UHF receiver unit (like an Hewlett Packard 'HP M1401A' mainframe), having one receiving channel for each transmitter. The received information is passed to a central display unit (like an Hewlett Packard 'HP 78560A Central Monitor'), where the information is displayed.

SpO2 measurement systems require a relatively high amount of electrical power. Therefore, SpO2 measuring has found only limited access to telemetric or handhold instruments, because in such a measurement environment, power is generally restricted to the battery life time.

One approach to employ SpO2 measurement while telemeter or handhold instruments are used is to simply measure SpO2 by separate stationary units, however, only manually and on demand. This approach cannot satisfy the demands of safe patient monitoring required in several applications.

Another approach to implement SpO2 measurement in telemetric or handhold instruments has been by using larger batteries. However, those large capacity batteries tend to be relatively costly and also heavy in weight, thus having a negative impact on the usability of those telemetry or handhold instruments.

SUMMARY OF THE INVENTION

It is an object of the invention to provide SpO2 measurement applicable in telemetric or handhold instruments.

According to the invention, the arterial oxygen saturation of hemoglobin (referenced herein as SpO2 measurement) is performed non-continuously in a so called intermittent mode, thus reducing the consumption of electrical energy and making it particularly applicable in telemetric or handhold instruments by increasing the battery life time. In this intermittent mode, SpO2 measurement is carried out, e.g., periodically according to a predetermined temporal test pattern, on demand, or according to any pre-given measuring profile.

It has to be understood, that the intermittent measuring is not limited to the measuring of only one SpO2 value at a certain moment, but can also comprise measuring multiple SpO2 values over a certain time interval. In the latter case, various analyzing methods as known in the art can be applied in order to determine an SpO2 value representative for that respective time interval or time period. The SpO2 value given out by the measuring device then indicates the SpO2 condition of the patient to a certain moment or representative for that time interval.

In a first embodiment, the SpO2 measurement is performed in a so called snap shot mode, whereby the SpO2 measuring is preferably carried out according to a predetermined time pattern, e.g., each minute. The snap shot mode leads to results representative for the actual SpO2 condition of the patient, when the measuring conditions are in a steady state and when the measured values are not influenced by side effects such as artifacts or movements of the patient.

According to a second embodiment, the SpO2 measurement is performed in a so called intelligent snap shot mode. A representative SpO2 value is first indicated, when the measured SpO2 value or values fulfil a certain confidence criterion. The confidence criterion decides whether the determined SpO2 value(s) can be regarded as representative for the present condition of the patient, or not. When the confidence criterion is not met during a running measuring interval, an SpO2 value is not given out for this interval or the interval will be continued until the confidence criterion is eventually met and a representative value can be indicated. Preferably, a confidence value is assigned to each determined SpO2 value.

The time between successive measuring intervals can be adapted to the time durance of the respective measuring interval, the indicated SpO2 value, the confidence value of the indicated SpO2 value, or to other suitable parameters. The time between successive measuring intervals can be, e.g., increased in order to save energy or decreased in order to more intensively monitor the patient. For example when the indicated SpO2 values only differ slightly and their respective confidence values show high confidence, the time between successive measuring intervals can be increased. On the other hand when the indicated SpO2 values significantly differ, their respective confidence values just pass the confidence criterion, or the confidence criterion is only met after a certain time period, the time between successive measuring intervals can be decreased.

According to a preferred embodiment, a new measuring interval is started according to a pre-given time scheme, e.g., a new measuring interval is started one minute after the start of the previous one. In case a representative SpO2 value cannot be determined before the successive measuring interval is due to be started, the running measuring can be continued until a representative SpO2 value is found, or a representative SpO2 value is not given out for that measuring interval and the successive measuring interval is started.

The confidence criterion can be predetermined as a fixed criterion or dependent on the measuring context, e.g., on the measuring history, the SpO2 values, or the time until the confidence criterion is met during a running measuring interval.

According to another preferred embodiment, the confidence value is determined by way of statistically analyzing the measured SpO2 values of each measuring interval. This is preferably accomplished by determining the standard deviation of the measured SpO2 values. However, any other analyses such as mean deviation or determination of the noise level of the signal or the perfusion indicator can be applied.

According to a further preferred embodiment, the confidence values are determined by a so called predicting stability method which enables to decrease the measuring time. The predicting stability method allows to predict the stability of single measured values already when only a few measured values are available which might not be sufficient for a collective analyzing, such as averaging. Therefore, the predicting stability method is preferably applied before the measured values are processed collectively, e.g., by averaging. The stability of single measured values might be determined by calculating the standard deviation or by other suitable methods as known in the art indicating a trend of the measured values.

According to the predicting stability method, an estimated stability of each measured value is assessed based on empirical knowledge about the measuring process. The empirical knowledge might include information about the measuring condition or the transient behavior of the measurement. In case the estimated stability of the individual measured values is satisfactory, a measuring result (e.g., the last measured value fulfilling the stability criterion and the stability value thereof) can be output and a collective processing, e.g., averaging, of the measured values is dispensable. Thus, the predicting stability method allows to reduce the measuring time without unduly jeopardizing the quality of the measuring result. A statement about the stability of the measured values can be derived from only a limited number of measured values which might not be enough for a collective processing. In case the estimated stability of the individual measured values is not satisfactory, the measured values might need to be further processed collectively.

BRIEF DESCRIPTION OF THE DRAWINGS

Other objects and many of the attendant advantages of the present invention will be readily appreciated and become better understood by reference to the following detailed description when considering in connection with the accompanied drawings, in which.

DETAILED DESCRIPTION OF THE INVENTION

Figure 1:
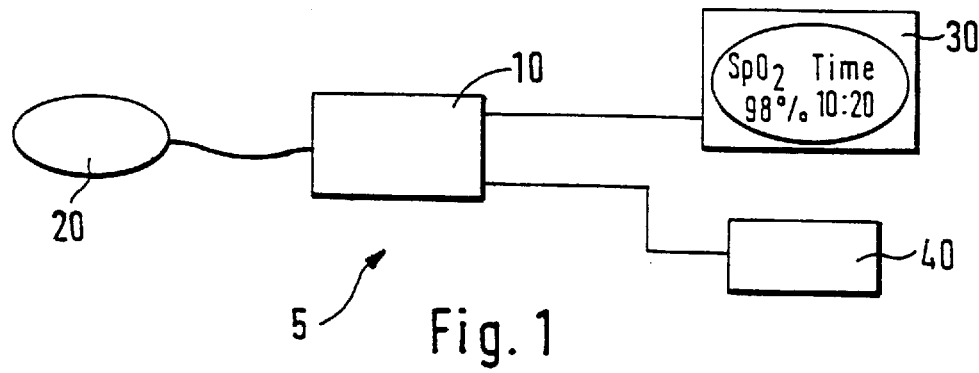
FIG. 1 shows a functional diagram of a SpO2 measuring unit according to the invention.

FIG. 1 shows a functional diagram of an SpO2 measuring unit 5 according to the invention. The SpO2 measuring unit 5 preferably comprises an SpO2 measuring device 10 connected to an SpO2 sensor 20, to a display unit 30, and to a controller unit 40. The SpO2 measuring device 10 receives measuring signals from the SpO2 sensor 20 and evaluates the received signals, as known in the art. The output of the SpO2 measuring device 10 can be displayed by the display unit 30. The controller unit 40 controls the powering of the SpO2 measuring device 10 and the SpO2 sensor 20 and thus the power consumption of the SpO2 measuring unit 5.

Preferably, the controller unit 40 is an Hewlett Packard 'HP M2601A Telemetric Transmitter' with an embedded SpO2 measurement device 10. The SpO2 sensor 20 can preferably be an Hewlett Packard 'SpO2 Adult Sensor HP M1191A' and the display unit 30 preferably is an Hewlett Packard 'HP 78560A Central Station' together with an 'HP M2604A Telemetric Receiver'.

In a handhold or telemetric application, the SpO2 measuring unit 5 is preferably supplied by batteries or accumulators (not shown in FIG. 1), which should last as long as possible to support a longest possible monitoring without battery exchanges.

According to the invention, SpO2 measurement is performed non-continuously in a so called intermittent mode, thus reducing the consumption of electrical energy and making it particularly applicable in telemeter or handhold instruments by increasing the battery life time. Powering on and off of the SpO2 measurement device 10 is controlled by the controller unit 40, preferably triggered by a request of the SpO2 measurement device 10 after it has communicated its intermittent measurement value to the display device 30. It is to be understood that the controller unit 40 can either be a part of the SpO2 measurement device 10 or separated therefrom. The powering of the SpO2 measurement device 10 controlled by the controller unit 40 can also be limited to only parts of the SpO2 measurement device 10.

The SpO2 measurement is preferably carried out periodically according to a predetermined temporal test pattern, however, can also be performed on demand, or according to any pre-given measuring profile. The intermittent SpO2 measuring can be executed by measuring only one SpO2 value at a certain moment, however, is preferably executed by measuring a plurality of SpO2 values over a certain time interval. In that case, various analyzing methods such as averaging can be applied in order to determine an SpO2 value representative for the respective time interval. The SpO2 values given out from the SpO2 measuring device 10 to the display device 30 then indicate—dependent on the measuring mode—the SpO2 condition of the patient to a certain moment or representative for a certain time interval.

In a first embodiment, the SpO2 measurement is performed in a so called snap shot mode, whereby the SpO2 measuring is preferably carried out or started according to a predetermined time pattern, e.g., once per minute. The measured value is then a 'snap shot' value of the current arterial oxygen saturation value. A value is derived each time the SpO2 measuring device 10 is powered. The simplest way to get an intermittent SpO2 value is by taking the first or the n-th measured SpO2 value available. However, this value might not be representative for the measurement interval or it can be disturbed by noise of movement artifacts.

According to a second embodiment, the SpO2 measurement is performed in a so called intelligent snap shot mode. A representative SpO2 value is first indicated, when the measured SpO2 value or values fulfil a certain confidence criterion. The confidence criterion decides whether the determined SpO2 value(s) can be regarded as representative for the present condition of the patient. When the confidence criterion is not met during a running measuring interval, an SpO2 value is not given out for this interval or the interval will be continued until the confidence criterion is eventually met and a representative value can be indicated.

When the confidence criterion is met and 'confident' values are derived, the SpO2 measuring device 10 is switched off, thus saving battery life time. When an error condition is realized the SpO2 measuring device 10 is also preferably powered down. The "power-on" time preferably depends as well on the signal quality as on the current state of the SpO2 trend. In that case, the measurement time will be longer, e.g., when the signal is noisy, the patient is ambulating or when the patient is being de-saturated.

It has been found that a better performance is reached, if more knowledge (and history) of the saturation measurement phase is available. Therefore, it is desirable to wait until more knowledge of the measurement phase is available to have a more confident intermittent SpO2 value.

According to the intelligent snap shot mechanism, knowledge is gathered not only about the SpO2 value itself but also about the confidence and stability of the saturation calculation algorithm. If the measurement condition is unstable, e.g., because of noise, artifacts or rapid saturation changes, the intelligent snap shot value will wait until a representative SpO2 value is available which might best cover the present oxygen saturation condition, or information about an error condition is signaled (for example that a pulse cannot be found).

The time between successive measuring intervals (successive interval time) or the time between the start of successive measuring intervals (successive start time) can be adopted, e.g., to the time durance of the respective measuring interval, the indicated SpO2 value, the confidence value of the indicated SpO2 value, or to other suitable parameters. The successive interval time—or the successive start time—can, e.g., be increased in order to save energy or decreased in order to more intensively monitor the patient. Preferably, when the indicated SpO2 values only differ slightly and their respective confidence values show high confidence, the successive interval time—or the successive start time—is increased. On the other hand, when the indicated SpO2 values differ significantly, their respective confidence values just pass the confidence criterion, or the confidence criterion is first met after a certain time period, the successive interval time—or the successive start time—is decreased.

The confidence criterion can be predetermined as a fixed criterion or dependent on the measuring context, e.g., on the measuring history, the SpO2 values, or the time until the confidence criterion is met during a measuring interval.

According to a preferred embodiment, the confidence value is determined by way of statistically analyzing the measured SpO2 values of each measuring interval. This is preferably accomplished by determining the standard deviation of the measured SpO2 values.

Figure 2:
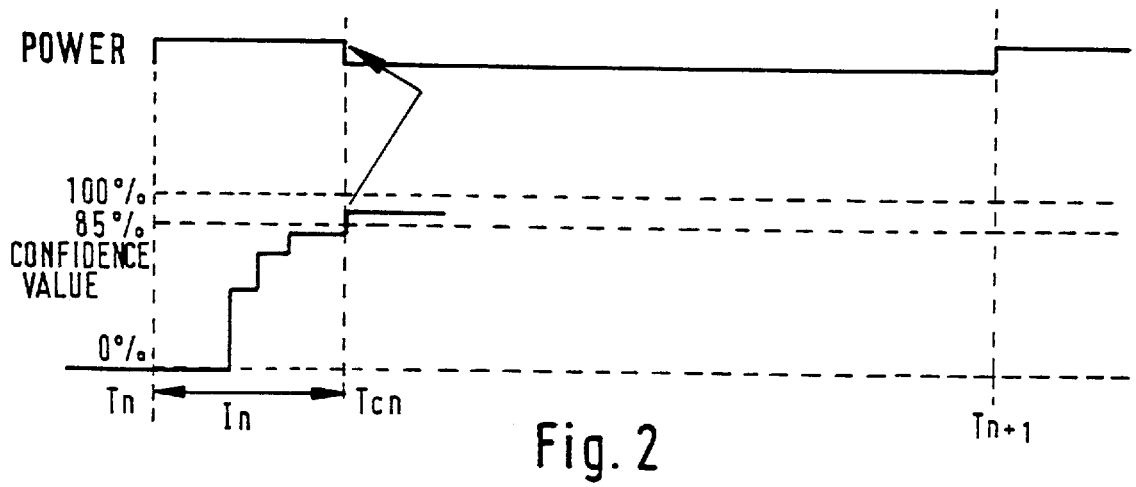
FIG. 2 shows an example of a start-up timing diagram for a 'good' signal which is relatively free from artifacts and has a high pulsating component.
Figure 3:
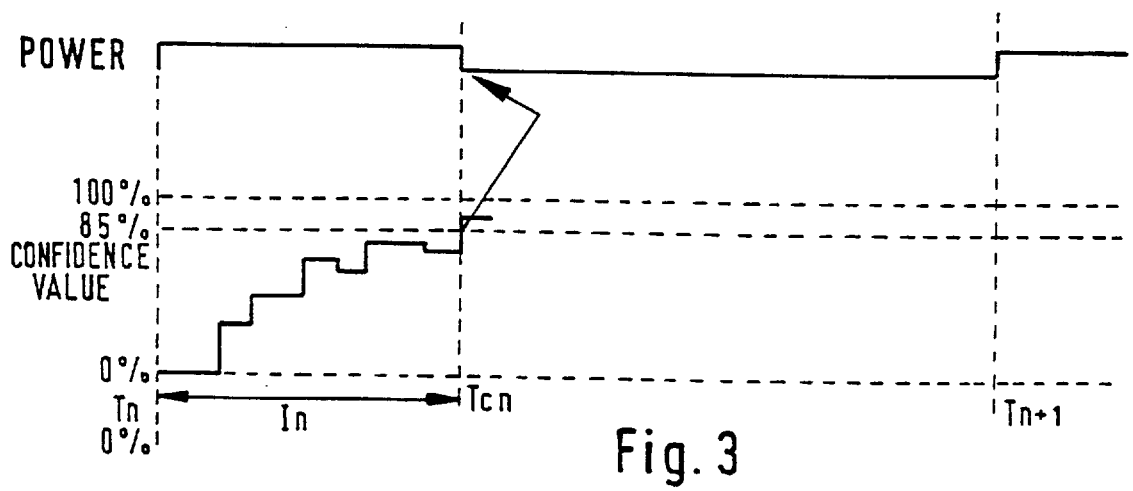
FIG. 3 shows an example of a start-up timing diagram for a 'poor' signal whose raw wave is not free of (movement) artifact or which has only a small pulsating component.

FIGS. 2 and 3 show examples of start-up timing diagrams, whereby FIG. 2 shows an example for a 'good' signal, that is a signal which is relatively free from artifacts and has a high pulsating component (high perfusion), and FIG. 3 shows an example for a 'poor' signal, that is a signal whose raw wave is not free of (movement) artifact or which has only a small pulsating component. A first measuring interval $I_n$ is started at a time Tn. The determined confidence value during the measuring interval $I_n$ is below a pre-given confidence criterion. The confidence can be understood, e.g., as a value between 0 and 100%, whereby 0% means no confidence and 100% means highest possible confidence. As a measured value always underlies some noise and artefacts, 100% confidence is not realistic. It was found, that 85% confidence is an adequate confidence limit for the end of a measurement interval.

In the examples in FIGS. 2 and 3, the confidence criterion is selected as 85%. As soon as the confidence value of the SpO2 measurement reaches the confidence criterion at a time Tcn, the controlling device 40 will switch off the SpO2 measurement device 10, preferably until a next measuring interval $I_{n+1}$ will be started at a time Tn+1. It will be seen that in case of the 'poor' signal as shown in FIG. 3, the time until confidence of the SpO2 measurement is reached will be longer as for the good signal in FIG. 2.

In a preferred embodiment, the confidence values are determined by employing the predicting stability method allowing to decrease the measuring time. Base for the determination of the confidence value are beat-to-beat SpO2 values, which are SpO2 values determined for each detected pulse before any filtering or averaging. According to the predicting stability method, the standard deviation of the beat-to-beat SpO2 values is first calculated. In parallel, the beat-to-beat SpO2 values are further processed, e.g., by filtering and averaging stages of the saturation calculation algorithm. In accordance with the predicting stability method, an estimated standard deviation of the SpO2 values received from the saturation calculation algorithm is assessed based on an empirical knowledge. The empirical knowledge preferably includes what kind of effect the filtering and averaging stages have on the beat-to-beat standard deviation.

The confidence value is interpolated to the estimated standard deviation in a way that 0% standard deviation is equal to 100% confidence, 1.5% standard deviation is 85% and greater than 10% standard deviation is 0% confidence. As soon as enough filtered and averaged SpO2 output values are available (e.g., 5 or more SpO2 values), the standard deviation, used for the confidence calculation, is not anymore based on the estimated standard deviation but directly calculated from the filtered and averaged SpO2 output values.

Other possible improvements to the intermittent mode performance using a buffered RAM and saving some knowledge from the last measurement interval can make a new measurement cycle faster (e.g., last SpO2 value, last standard deviation (STD), last pulse rate, last control parameters, last confidence value). This buffered values can be used after a start-up of the measurement device as start values. The last SpO2 value could be used as first value for the started measurement interval. This saves one beat of the running measurement interval. Other information beside the last SpO2 value could help to adjust the confidence calculation as additional parameters, e.g., increase the calculated confidence if the last estimated STD was similar to the new calculated.

In a further embodiment, the derived confidence may incorporate other available information from the saturation calculation algorithm, such as the number of detected beats versus pulse rate, the correlation between red and infrared waves, detected artifacts, pending error conditions, noise of the raw signals etc.

In a further embodiment, the intermittent mode is designed in a way that if an intermittent measurement value is available, the SpO2 measurement device 10 switches under certain circumstances automatically to a continuous measurement. Such circumstances can be, for example, when a de-saturation occurred. The measurement may be kept powered and without an interruption, the measurement device will continue to communicate continuous SpO2 values.

According to another embodiment, a clinician can select, whether intermittent SpO2 measurement will be applied to a patient or not. The device can be configured to do the SpO2 measurement continuously (with a reduced battery life time) or intermittent (with a longer battery lifetime).

The confidence calculation, is preferably based on statistical analysis of the beat-to-beat SpO2 values of the saturation calculation algorithm. However, if a different saturation calculation algorithm is used in the measurement device (for example a different saturation calculation algorithm), this saturation calculation algorithm might not be based on pulse finding and beat-to-beat processing. Other methods of SpO2 calculation are based on signal analysis of the red and infrared raw wave using a time window (eg. correlation or fast Fourier transformation). If such an SpO2 saturation calculation algorithm method is used, there are no beat-to-beat values available for the STD calculation. In this case, the saturation calculation algorithm should start with a minimum time window for signal analysis. The SpO2 values calculated on this minimum time window could then further be regarded as beat-to-beat SpO2 values and further processed as mentioned herein.

In a further preferred embodiment, the measured SpO2 values are only updated on the display device 30 after a new representative SpO2 value has been determined. However, the indicated SpO2 value is preferably displayable by the display device 30 even if the SpO2 measurement device 10 is switched off. Beside the SpO2 value, the display device may also give reference to the respective measuring time, e.g., by indicating the measuring time of the last displayed SpO2 value. This is exemplarily demonstrated in FIG. 1.

I claim:

1. A system for detecting blood oxygenation, comprising a measuring device for performing a blood oxygenation measurement and a controller unit, characterized in that the measuring device is controlled by the controller unit, said controller unit responsive to a measured value from said measuring device reaching a threshold value to disable operation of said measuring device and to re-enable said measuring device upon a further criteria being reached, whereby the blood oxygenation measurement is performable non-continuously.

2. The system of claim 1, further comprising means for periodically carrying out the blood oxygenation measurement in accordance with a predetermined temporal test pattern or on demand.

3. The system of claim 1, further comprising means for indicating a representative blood oxygenation value, when one or more measured blood oxygenation values fulfil a pre-given confidence criterion.

4. The system of claim 1, further comprising means for adapting the time between successive measuring intervals or for adapting the time between the start of successive measuring intervals to the time durance of a respective measuring interval, an indicated blood oxygenation value, or to a confidence value of the indicated blood oxygenation value.

5. The system of claim 1, further comprising means for statistically analyzing the measured blood oxygenation values measured during a measuring interval.

6. A method for detecting blood oxygenation, through use of a measuring device for performing a blood oxygenation measurement and a controller unit, said method comprising the steps of:

a) controlling the measuring device is to make blood oxygen measurements;

b) disabling operation of said measuring device upon a measured value from said measuring device reaching a threshold value; and c) re-enabling said measuring device upon a further criteria being reached, whereby the blood oxygenation measurement is performed non-continuously.

7. The method of claim 12, wherein step a) comprises a first step of powering on a measuring device for performing a blood oxygenation measurement, a second step of performing the blood oxygenation measurement, and step b) comprises a third step of powering down the measuring device or parts thereof, whereby the three steps are repeatable periodically.

8. The method of claim 12, wherein the time between successive measuring intervals is adapted to the time duration of a respective measuring interval, an indicated blood oxygenation value, or to a confidence value of the indicated blood oxygenation value.

9. The method of claim 13, further comprising prior to the third step a step of statistically analyzing the measured blood oxygenation values measured during each measuring interval.

10. The method of claim 13, further comprising a step prior to the third step of indicating a blood oxygenation value representative for a measured time interval.

11. The method of claim 13, wherein the second step comprises a step of predicting the stability of measured blood oxygenation values by
   a) determining individual beat-to-beat blood oxygenation values,
   b) assessing an estimated standard deviation for the blood oxygenation values based on empirical knowledge,
   c) interpolating the confidence value to the estimated standard deviation.

12. A method for detecting blood oxygenation, characterized in that the measuring of the blood oxygenation is performed non-continuously.

13. A method of claim 12, comprising a first step of powering on a measuring device for performing a blood oxygenation measurement, a second step of performing the blood oxygenation measurement, a third step of powering down the measuring device or parts thereof, whereby the three steps are repeatable periodically.

14. The method of claim 12, wherein the blood oxygenation measurement is carried out periodically according to a predetermined temporal test pattern or on demand.

15. The method of claim 13, wherein the blood oxygenation measurement is carried out periodically according to a predetermined temporal test pattern or on demand.

16. The method of claim 12, wherein a representative blood oxygenation value is indicated when one or more measured blood oxygenation values fulfil a pre-given confidence criterion.

17. The method of claim 12, wherein the time between successive measuring intervals is adapted to the time durance of a respective measuring interval, an indicated blood oxygenation value, or to a confidence value of the indicated blood oxygenation value.

18. The method of claim 12, further comprising prior to the third step a step of statistically analyzing the measured blood oxygenation values measured during each measuring interval.

19. The method of claim 18, wherein the step of statistically analyzing the measured blood oxygenation values comprises a step of determining the standard deviation of the measured blood oxygenation values.

20. The method of claim 12, further comprising a step prior to the third step of indicating a blood oxygenation value representative for a measured time interval.

21. The method of claim 20, wherein the step of indicating a blood oxygenation value is first executed when the confidence criterion is met.

22. The method of claim 12, wherein the second step comprises a step of predicting the stability of measured blood oxygenation values by
   a) determining individual beat-to-beat blood oxygenation values,
   b) assessing an estimated standard deviation for the blood oxygenation values based on empirical knowledge,
   c) interpolating the confidence value to the estimated standard deviation.

23. The method of claim 22, wherein the step of predicting the stability of measured blood oxygenation values is executed until enough measured blood oxygenation values are available for a collective processing.

24. The method of claim 12, wherein the time between successive measuring intervals or the time between the start of successive measuring intervals is increased when the indicated blood oxygenation values only differ slightly and their respective confidence values show high confidence, and/or decreased when the indicated blood oxygenation values differ significantly, their respective confidence values just pass the confidence criterion, or the confidence criterion is first met after a certain time period.

* * * * *